United States Patent [19]

Ogawa et al.

[11] Patent Number: 4,579,783
[45] Date of Patent: Apr. 1, 1986

[54] ELEMENT FOR ELECTROPHORESIS

[75] Inventors: Masashi Ogawa; Hisashi Shiraishi; Teppei Ikeda, all of Minami-ashigara, Japan

[73] Assignee: Director of The Finance Division, Minister's Secretariat, Science & Technology Agency, Tokyo, Japan

[21] Appl. No.: 611,594

[22] Filed: May 18, 1984

[30] Foreign Application Priority Data

May 19, 1983 [JP] Japan .................................. 58-87967

[51] Int. Cl.$^4$ ............................................. B32B 27/28
[52] U.S. Cl. .............................. 428/475.2; 204/299 R; 204/182.8; 428/483; 524/521; 526/287
[58] Field of Search ....................... 204/299 R, 180 G; 526/287; 428/483, 475.2; 524/521

[56] References Cited

U.S. PATENT DOCUMENTS 4,319,975   3/1982   Cook ................................ 204/299 R
4,415,428   11/1983  Nochumson et al. .......... 204/299 R Primary Examiner—Edith Buffalow
Attorney, Agent, or Firm—Toren, McGeady, Stanger, Goldberg & Kiel

[57] ABSTRACT

An element for electrophoresis comprising the following three-layer structure laminated in the order:
 (I) a support layer;
 (II) an adhesive layer comprising a copolymer having at least one specifically selected repeating unit; and
 (III) a medium layer for electrophoresis comprising an aqueous polyacrylamide gel formed by crosslinking polymerization of an acrylamide compound and a crosslinking agent in the presence of water, and a compound containing at least one carbamoyl group (modifier).

6 Claims, No Drawings

ELEMENT FOR ELECTROPHORESIS

BACKGROUND OF OF THE INVENTION

1. Field of the Invention

This invention relates to an element for electrophoresis, and more particularly relates to an element for electrophoresis suitably employable for determination of base sequence of DNA, RNA, their fragments, and their derivatives.

2. Description of Prior Arts

In the method for determination of the base sequence of DNA, RNA, their fragments, and their derivatives according to the post-label method, the operation of slab electrophoresis using a polyacrylamide gel membrane has become essential. Since the study in the genetic engineering technology has advance recently, quick determination of the base sequence of DNA, etc. is highly desired.

The polyacrylamide gel membrane employable for the above purpose can be prepared by crosslinking polymerization of a monomer such as acrylamide and a two-functional crosslinking agent such as N,N'-methylenebisacrylamide under an oxygen-free condition in the presence of water and a polymerization catalyst. In the course of the preparation of the polyacrylamide gel membrane, a modifier such as urea or formamide is generally incorporated into the membrane.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3-1 mm); sealing the gel-forming solution from oxygen; and causing the crosslinking polymerization to prepare the desired gel membrane. The procedure employing the glass plates are disadvantageous because the glass plate is easily breakable and rather heavy, and careful handling is accordingly required. Thus, the above procedure employing the glass plates is difficultly utilized to prepare the polyacrylamide gel membranes in a mass scale.

The polyacrylamide gel membrane prepared as above is employed for electrophoresis in the manner such as described below.

The polyacrylamide gel membrane is vertically placed in the form of being sandwiched between the glass plates, and in the first place a pre-electrophoresis operation is carried out. Then, a certain amount of a sample ($^{32}$P-labeled DNA cleaved by Maxam-Gilbert method) is introduced into sample slots provided on the membrane, and electrophoresis is carried out. After the electrophoresis is carried out for a certain period of time (e.g., approx. 6-12 hours), one glass plate is removed carefully and the exposed gel membrane is covered with a polymer film such as poly(vinylidene chloride) for being subjected to autoradiographic process. The autoradiographic process is carried out by the following procedures: A radiographic film and an intensifying screen are superposed successively on the film covering the gel membrame, whereby exposing the radiographic film to the gel membrane at a low temperature (e.g., −80° C.) for a certain period of time (e.g., approx. 10-20 hours). After the exposing procedure, the radiographic film is developed, and the resolved pattern reproduced on the film is studied for determination of the base sequence of DNA, etc.

Since the autoradiographic process requires a long period as described above, it has been desired that the operation period is shortened. Moreover, enhancement of resolution accuracy in the detection of the resolved pattern is desired.

It is known that the resolution accuracy can be enhanced by applying the autoradiographic process to the gel membrane in dry state. The procedure for drying the gel membrane can be carried out as follows. The gel membrane having been subjected to electrophoresis is immersed in 10% aqueous acetic acid solution so as to fix the resolved DNA cleavage products as well as to remove the modifier such as urea from the membrane. The adhesion between the glass plate and the gel membrane is weak or nelgigible, the gel membrane easily separates from the glass plate and floats in the solution. The separated gel membrane is carefully taken out, placed on a filter paper, and dried under reduced pressure. The membrane is thus dried and fixed onto the filter paper. The autoradiographic process applied to the dry membrane shows highly enhanced resolution. However, the drying process has such drawbacks that the separation and drying stages require highly trained skill and careful handling and actually the membrane is sometimes broken in these stages.

SUMMARY OF THE INVENTION

An object of the present invention is to provide a element for electrophoresis which is improved in the adhesion between the support and the polyacrylamide gel medium such as in the form of a membrane.

Another object of the present invention is to provide a element for electrophoresis which is substantially free from sepration between the polyacrylamide gel medium and the support in the course of a stage for removing modifier (e.g., urea) and a subsequent drying stage.

There is provided by the present invention a element for electrophoresis comprising the following three-layer structure laminated in the order:

(I) a support layer;
(II) an adhesive layer comprising a polymer having at least one repeating unit selected from the group consisting of:
(1) a repeating unit having the formula (1):

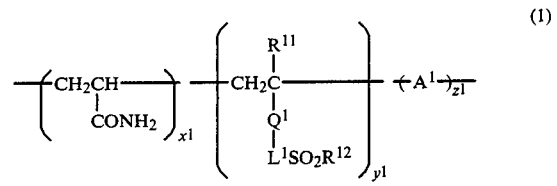

in which $R^{11}$ is the hydrogen atom or an alkyl group containing 1-6 carbon atoms; $Q^1$ is —COO—, —CON($R^{11}$)—, or an arylene group containing 6-10 carbon atoms; $L^1$ is a divalent group containing at least one linkage selected from the group consisting of —COO— and —CON($R^{11}$)— and containing 3-15 carbon atoms, or a divalent group containing at least one linkage selected from the group consisting of —O—, —N($R^{11}$)—, —CO—, —SO—, —$SO_2$—, —$SO_3$—, —$SO_2N(R^{11})$—, —$N(R^{11})CON(R^{11})$— and —$N(R^{11})COO$—, and containing 1–12 carbon atoms, in which $R^{11}$ has the same meaning as defined above; $R^{12}$ is —CH=$CH_2$ or —$CH_2CH_2X^1$, in which $X^1$ is a substituent replaceable with a nucleophilic group or releasable in the form of $HX^1$ by a base; $A^1$ is a divalent group derived from an ethylenic unsaturated monomer copolymerizable with monomers forming other unit portions; and $x^1$, $y^1$ and $z^1$ all representing molar percents range from 0 to 99, from 1 to 99, and from 1 to 99, respectively;

(2) a repeating unit having the formula (2):

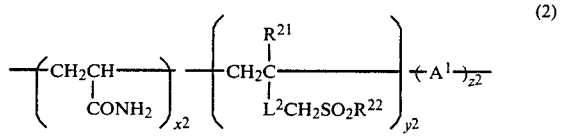

in which $R^{21}$ is the hydrogen atom or an alkyl group containing 1–6 carbon atoms; $R^{22}$ is —CH=$CH_2$ or —$CH_2CH_2X^2$, in which $X^2$ is a substituent replaceable with a nucleophilic group or releasable in the form of $HX^2$ by a base; $L^2$ is a divalent group selected from the group consisting of an alkylene group containing 1–6 carbon atoms, an arylene group containing 6–12 carbon atoms, —$COZ^2$—, and —$COZ^2R^{23}$—, in which $R^{23}$ is an alkylene group containing 1–6 carbon atoms, or an arylene group containing 6–12 carbon atoms, and $Z^2$ is the oxygen atom or NH; $A^2$ is a divalent group derived from an ethylenic unsaturated monomer copolymerizable with monomers forming other unit portions; and $x^2$, $y^2$ and $z^2$ all representing molar percents range from 0 to 99, from 1 to 99, and from 1 to 99, respectively; and (3) a repeating unit having the formula (3):

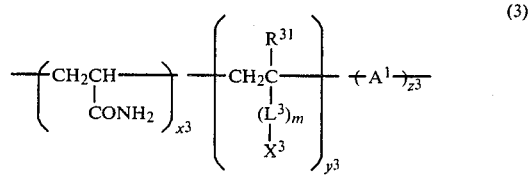

in which $R^{31}$ is the hydrogen atom or an alkyl group containing 1–6 carbon atoms; $L^3$ is a divalent linkage group containing 1–20 carbon atoms; $X^3$ is an active ester; $A^3$ is a divalent group derived from an ethylenic unsaturated monomer copolymerizable with monomers forming other unit portions; and $x^3$, $y^3$ and $z^3$ all representing molar percents range from 0 to 99, from 1 to 99, and from 1 to 99, respectively; and m is 0 or 1; and (III) a medium layer for electrophoresis comprising an aqueous polyacrylamide gel formed by cross-linking polymerization of an acrylamide compound and a crosslinking agent in the presence of water, and a compound containing at least one carbamoyl group serving as modifier.

The element for electrophoresis of the present invention comprises a three-layer structure in which the support layer and the medium layer are combined by means of the specific adhesive layer. This three-layer structure hardly separates in the course of a variety of operations performed in the aforementioned drying stage. Accordingly, the medium (or membrane) is hardly broken in the handling. Further, no filter paper is needed in the autoradiographic process.

Moreover, the element for electrophoresis of the present invention can be prepared by forming the adhesive layer on a horizontally placed support and subsequetnly forming the medium layer thereon. Therefore, the element for electrophoresis of the invention is advantageously prepared in a mass scale.

DETAILED DESCRIPTION OF THE INVENTION

Examples of the support employable for the preparation of the element for electrophoresis of the present invention include glass plate, paper sheet and a variety of plastic material sheets. The support of plastic material sheet is preferably employed to effectively utilize the advantageous feature of the present invention. The plastic material sheet can be made of an optionally selected material, but a polyethylene terephthalate sheet is preferably employed.

DESCRIPTION ON THE ADHESIVE LAYER

According to the present invention, an adhesive layer is provided on the support.

The adhesive layer comprises a polymer having at least one repeating unit selected from the group consisting of the following repeating units represented by the formulae (1), (2) and (3).

(1) A repeating unit having the formula (1):

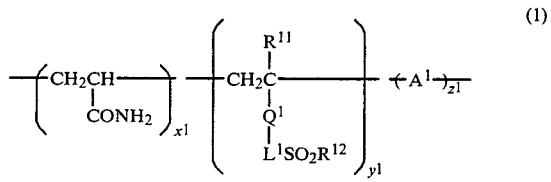

in which $R^{11}$ is the hydrogen atom or an alkyl group containing 1–6 carbon atoms; $Q^1$ is —COO—, —CON($R^{11}$)—, or an arylene group containing 6–10 carbon atoms; $L^1$ is a divalent group containing at least one linkage selected from the group consisting of —COO— and —CON($R^{11}$)— and containing 3–15 carbon atoms, or a divalent group containing at least one linkage selected from the group consisting of —O—, —N($R^{11}$)—, —CO—, —SO—, —$SO_2$—, —$SO_3$—, —$SO_2N(R^{11})$—, —$N(R^{11})CON(R^{11})$— and —$N(R^{11})COO$—, and containing 1–1 carbon atoms, in which $R^{11}$ has the same meaning as defined above; $R^{12}$ is —CH=$CH_2$ or —$CH_2CH_2X^1$, in which $X^1$ is a substituent replaceable with a nucleophilic group or releasable in the form of $HX^1$ by a base; $A^1$ is a divalent group derived from an ethylenic unsaturated monomer copolymerizable with monomers forming other unit portions (shown in the left therefrom); and $x^1$, $y^1$ and $z^1$ all representing molar percents range from 0 to 99, from 1 to 99, and from 1 to 99, respectively.

Examples of $R^{11}$ in the above formula (1) include methyl, ethyl, butyl and n-hexyl groups.

Examples of $Q^1$ include —COO—, —CONH—, —$CON(CH_3)$—, —$CON(C_2H_5)$—, —$CON(n-C_4H_9)$—,

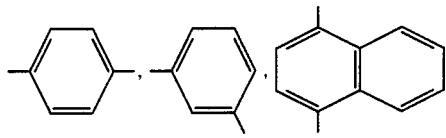

Examples of $L^1$ include the following divalent groups, which can be arranged in any direction within the formula (1), so far as it can connect $Q^1$ and $SO_2$: —CH$_2$COOCH$_2$—, —CH$_2$COOCH$_2$CH$_2$—, —CH$_2$CH$_2$COOCH$_2$—, —(CH$_2$)$_5$COOCH$_2$CH$_2$—, —(CH$_2$)$_{10}$COOCH$_2$CH$_2$—, —CH$_2$NHCOCH$_2$—, —CH$_2$NHCOCH$_2$CH$_2$—, —(CH$_2$)$_3$NHCOCH$_2$CH$_2$—, —(CH$_2$)$_5$NHCOCH$_2$CH$_2$—, —(CH$_2$)$_{10}$NHCOCH$_2$CH$_2$—, —CH$_2$OCH$_2$—, —CH$_2$CH$_2$OCH$_2$CH$_2$CH$_2$—, —N(CH$_3$)CH$_2$CH$_2$—, —CH$_2$N(CH$_3$)CH$_2$CH$_2$—COCH$_2$CH$_2$—, —CH$_2$COCH$_2$CH$_2$—,

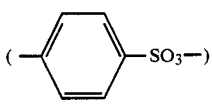

—SOCH$_2$CH$_2$—, —CH$_2$SOCH$_2$CH$_2$—, —SO$_2$CH$_2$CH$_2$—, —SO$_2$CH$_2$CH$_2$SO$_2$CH$_2$CH$_2$—, —SO$_2$CH$_2$CH$_2$SO$_2$CH$_2$CH(OH)CH$_2$—, —SO$_3$CH$_2$CH$_2$CH$_2$—, —SO$_3$CH$_2$COOCH$_2$CH$_2$—, —SO$_3$CH$_2$CH$_2$COOCH$_2$CH$_2$—, —SO$_2$NHCH$_2$COOCH$_2$CH$_2$—, —SO$_2$NHCH$_2$CH$_2$COOCH$_2$CH$_2$—, —NHCONHCH$_2$CH$_2$—, —CH$_2$NHCONHCH$_2$CH$_2$—, —NHCOOCH$_2$CH$_2$—, and —CH$_2$NHCOOCH$_2$CH$_2$—.

$R^{12}$ is —CH=CH$_2$ or —CH$_2$CH$_2$X$^1$. Examples of $X^1$ include:

halogen atoms such as chlorine and bromine;

hydroxy group;

alkylsulfonyloxy groups such as methylsulfonyloxy (H$_3$CSO$_3$—), ethylsulfonyloxy, and propylsulfonyloxy;

arylsulfonyloxy groups such as phenylsulfonyloxy

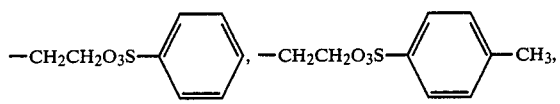

and p-tolylsulfonyloxy; and alkylcarbonyloxy groups such as acetoxy, propionyloxy, trifluoromethylcarbonyloxy and dichloromethylcarbonyloxy. Accordingly, examples of $R^{12}$ include the following groups: —CH=CH$_2$, —CH$_2$CH$_2$Cl, —CH$_2$CH$_2$Br, —CH$_2$CH$_2$O$_3$SCH$_3$, —CH$_2$CH$_2$O$_3$S—⟨phenyl⟩, —CH$_2$CH$_2$O$_3$S—⟨phenyl⟩—CH$_3$, —CH$_2$CH$_2$OH, —CH$_2$CH$_2$OOCCH$_3$, —CH$_2$CH$_2$OOCCF$_3$, and —CH$_2$CH$_2$OOCCHCl$_2$.

Examples of the divalent group represented by $A^1$ include groups derived from the following ethylenic unsaturated monomers: ethylene, propylene, 1-butene, isobutene, styrene, chloromethylstyrene, hydroxymethylstyrene, sodium vinylbenzenesulfonate, sodium vinylbenzylsulfonate, N,N,N-trimethyl-N-vinylbenzylammonium chloride, N,N-dimethyl-N-benzyl-N-vinylbenzylammonium chloride, α-methylstyrene, vinyltoluene, 4-vinylpyridine, 2-vinylpyridine, benzylvinylpyridinium chloride, N-vinylacetamide, N-vinylpyrrolidone, 1-vinyl-2-methylimidazole, mono-ethylenic unsaturated esters of aliphatic carboxylic acid (e.g., vinyl acetate and allyl acetate), ethylenic unsaturated monocarboxylic acids or dicarboxylic acids and salts thereof (e.g., acrylic acid, methacylic acid, itaconic acid, maleic acid, sodium acrylate, potassium acrylate, sodium methacrylate), maleic anhydride, esters of ethylenic unsaturated monocarboxylic acids or dicarboxylic acids (e.g., n-butyl acrylate, n-hexyl acrylate, hydrdoxyethyl acrylate, cyanoethyl acrylate, (diethylamino)ethyl acrylate, methyl methacrylate, n-butyl methacrylate, benzyl methacrylate, hydroxyethyl methacrylate, chloroethyl methacrylate, methoxyethyl methacrylate, (diethylamino)ethyl methacrylate, N,N,N-triethyl-N-methacryloyloxyethylammonium p-toluenesulfonate, N,N-diethyl-N-methyl-N-methacryloyloxyethylammonium p-toluenesulfonate, dimethyl itaconate, and monobenzyl maleate), amides of ethylenic unsaturated monocarboxylic acid or dicarboxylic acid (e.g., N,N-dimethylacrylamide, N-methylolacrylamide, and N-[(dimethylamino)propyl]acrylamide), N,N,N-trimethyl-N-(acryloylpropyl)ammonium p-toluenesulfonate, sodium 2-acrylamide-2-methylpropanesulfonate, acryloylmorpholine, methacrylamide, N,N-dimethyl-N'-acryloylpropanediamine propionate betaine, and N,N-dimethyl-N'-methacryloylpropanediamine acetate betaine.

In the case that the acrylamide copolymer of the invention is employed in the form of a crosslinked latex, $A^1$ can be other groups derived from monomers containing at least two copolymerizable ethylenic unsaturated groups (e.g., divinyl benzene, methylenebisacrylamide, ethyleneglycol diacrylate, triemthylene glycol diacrylate, ethyleneglycol dimethacrylate, trimethylene glycol dimethacrylate, neopentylglycol dimethacrylate, etc.).

(2) A repeating unit having the formula (2):

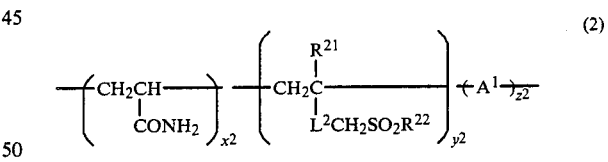

in which $R^{21}$ is the hydrogen atom or an alkyl group containing 1–6 carbon atoms; $R^{22}$ is —CH=CH$_2$ or —CH$_2$CH$_2$X$^2$, in which $X^2$ is a substituent replaceable with a nucleophilic group or releasable in the form of HX$^2$ by a base; $L^2$ is a divalent group selected from the group consisting of an alkylene group containing 1–6 carbon atoms (e.g., methylene, ethylene, and isobutylene), an arylene group containing 6–12 carbon atoms (e.g., phenylene, tolylene, and naphthalene), —COZ$^2$—, and —COZ$^2$R$^{23}$—, in which $R^{23}$ is an alkylene group containing 1–6 carbon atoms, or an arylene group containing 6–12 carbon atoms, and $Z^2$ is the oxygen atom or NH; $A^2$ is a divalent group derived from an ethylenic unsaturated monomer copolymerizable with monomers forming other unit portions; and $x^2$, $y^2$ and $z^2$ all representing molar percents range from 0 to 99, from 1 to 99, and from 1 to 99, respectively;.

In the formula (2), examples of $R^{21}$, $R^{22}$ and $A^2$ include the respective groups listed for $R^{11}$, $R^{12}$ and $A^1$ of the formula (1).

(3) A repeating unit having the formula (3):

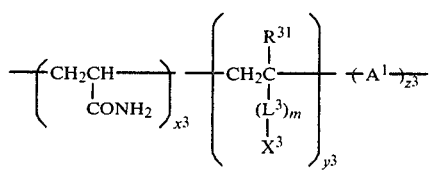
(3)

in which $R^{31}$ is the hydrogen atom or an alkyl group containing 1–6 carbon atoms; $L^3$ is a divalent linkage group containing 1–20 carbon atoms; $X^3$ is an active ester; $A^3$ is a divalent group derived from an ethylenic unsaturated monomer copolymerizable with monomers forming other unit portions; and $x^3$, $y^3$ and $z^3$ all representing molar percents range from 0 to 99, from 1 to 99, and from 1 to 99, respectively; and m is 0 or 1.

In the formula (3), examples of $R^{31}$ and $A^3$ include the groups listed for $R^{11}$ and $A^1$ of the formula (1).

Examples of $L^3$ include the following groups:
—COCH$_2$—, —COCH$_2$CH$_2$OCOCH$_2$CH$_2$—, —CONHCH$_2$—, —CONHCH$_2$CH$_2$—, —CONHCH$_2$CH$_2$CH$_2$—, —CONHCH$_2$CH$_2$CH$_2$CH$_2$CH$_2$—, —CONHCH$_2$CONHCH$_2$—, CONHCH$_2$CONHCH$_2$CONHCH$_2$—, —CONHCH$_2$NHCOCH$_2$CH$_2$CH$_2$SCH$_2$CH$_2$—, and —CONHCH$_2$OCOCH$_2$CH$_2$—.

Examples of $X^3$ include the following groups:

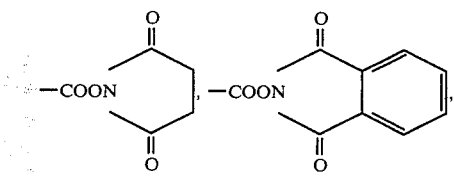

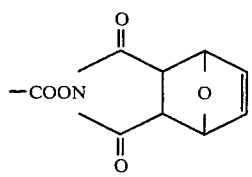

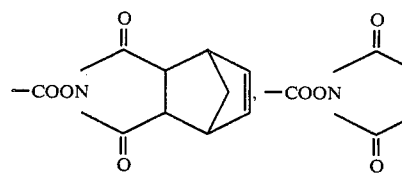

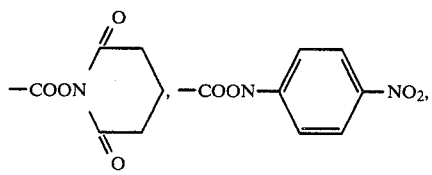

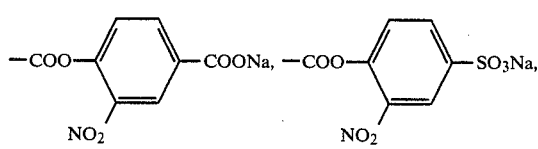

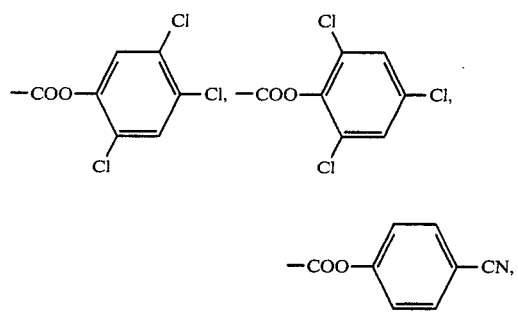

—COOCH$^2$CN, —COOCH$_2$COOC$_2$H$_5$, —COOCH$_2$CONH$_2$, —COOCH$_2$COCH$_3$,

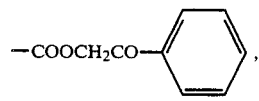

—COOCH$_2$COOCH=CH$_2$, —COON=CHCH$_3$, —COON=C(CH$_3$)$_2$, —COOC(CH$_3$)=CHCOCH$_3$,

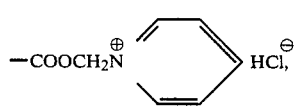

—COOCH$_2$CH$_2$Br, —COOCH$_2$CH$_2$CN, and —COOCH$_2$CH$_2$N$^\oplus$(CH$_3$)$_2$CH$_3$Cl$^\ominus$.

Processes for synthesis of representative ethylenic unsaturated monomers containing a vinylsulfonyl groups or a functional group convertible into a vinylsulfonyl group which are employable for the preparation of the polymers comprising the repeating unit represented by the formula (1), (2) or (3) are illustrated below.

SYNTHESIS EXAMPLE 1

Synthesis of 2-[3-(2-chloroethylsulfonyl)propionyloxy]ethyl acrylate

Into a mixture of 600 ml. of tetrahydrofuran, 45.8 g. of hydroxyethyl acrylate, and 72 g. of 3-(2-chloroethylsulfonyl)propionyl chloride placed in a reaction vessel chilled with ice-water to maintain the temperature below 5° C., a solution of 31.2 g. of pyridine in 100 ml. of tetrahydrofuran was poured dropwise for 1.75 hours. The resulting mixture was stirred at room temperature for 2 hours, and poured into 2.5 l. of ice-water. The aqueous mixture was then extracted with 4 portions of 300 ml. of chloroform. The organic extract was dried over sodium sulfate, and concentrated to give 87 g. of 2-[3-(2-chloroethylsulfonyl)propionyloxy]ethyl acrylate (yield 88%).

SYNTHESIS EXAMPLE 2

Synthesis of N-[3-(2-chloroethylsulfonyl)propanamidomethyl]acrylamide

CH$_2$=CHCONHCH$_2$NHCOCH$_2$CH$_2$SO$_2$CH$_2$CH$_2$Cl

In a 2-l. reaction vessel, 1,400 ml. of distilled water, 244 g. of sodium sulfite and 220 g. of sodium hydrogencarbonate were stirred to give a solution. To the resulting solution chilled with ice-water to maintain the temperature at approx. 5° C. was dropwise added for 1.5 hours 260 g. of chloroethanesulfonyl chloride. To the resulting mixture was further added dropwise for approx. 15 min. 160 g. of 49% sulfuric acid. The mixture was then stirred at 5° C. for 1 hour, and the produced crystalline precipitate was filtered off. The precipitate was then washed with 400 ml. of distilled water. The filtrate and the water collected from the washing were together introduced into a 3-l. reaction vessel. Into the reaction vessel chilled with ice to maintain the temperature at approx. 5° C. was dropwise added for 30 min. a solution of 246 g. of methylenebisacrylamide in a mixture of 480 ml. of distilled water and 1,480 ml of ethanol. The reaction vessel was then stored in a refrigerator for 5 days to complete the reaction. The precipitated crystals were collected by filtration and washed with 800 ml. of chilled distilled water. The crystals were then recrystallized from 2,000 ml. of 50% aqueous ethanol to give 219 g. of the desired monomer: yield 49%. Analysis: H 5.17%; C 37.90%; N 9.48%; Cl 12.58%.

SYNTHESIS EXAMPLE 3

Synthesis of [3-(2-chloroethylsulfonyl)propanamido]methylstyrene

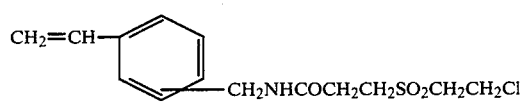

Into a mixture of 100 ml. of tetrahydrofuran, 20.1 g. of vinylbenzylamine, 16.7 g. of triethylamine, and 0.1 g. of hydroquinone placed in a reaction vessel chilled with ice-water a solution of 36.1 g. of β-chloroethylsulfonyl-propionyl chloride in 200 ml. of tetrahydrofuran was poured dropwise for 30 min. The resulting mixture was allowed to stand overnight at room temperature. Subsequently, the mixture was poured into a diluted sulfuric acid prepared from 16.5 g. of conc. sulfuric acid and 1.5 l. of ice-water. The produced precipitate was collected by filtration. The collected precipitate was recrystallized from a mixture of 200 ml. of ethanol and 200 ml. of water to give 26.8 g. of [3-(2-chloroethylsulfonyl)-propanamido]methyl styrene: yield 57%. Analysis: H 5.74%; C 53.47%; N 4.83%; Cl 10.99%; S 10.49%.

SYNTHESIS EXAMPLE 4

Synthesis of 1-[2-(4-vinylphenylsulfonyl)ethylsulfonyl]-3-(2-chloroethyl)sulfonyl-2-propanol

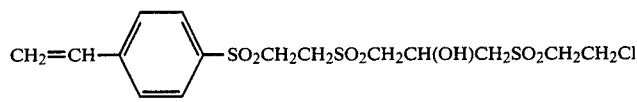

CH$_2$=CH—C$_6$H$_4$—SO$_2$CH$_2$CH$_2$SO$_2$CH$_2$CH(OH)CH$_2$SO$_2$CH$_2$CH$_2$Cl

To a mixture of 157 g. of 1,3-bis(2-chloroethyl)sulfonyl-2-propanol (prepared by the method disclosed in Japanese Patent Provisional Publication No. 53(1978)-57257), 1 l. of methanol and 1 l. of distilled water placed in a reaction vessel and heated to 46° C. was dropwise added for 1 hour a solution of 52 g. of potassium vinylbenzenesulfinate in a mixture of 100 ml. of methanol and 100 ml. of distilled water. The resulting mixture was further stirred at 46° C. for 5.5 hours. The produced precipitate was collected to give 55 g. of 1-[2-(4-vinylphenylsulfonyl)ethylsulfonyl]-3-(2-chloroethyl)sulfonyl-2-propanol: yield 49%. Analysis: H 4.67%; C 39.89%; S 21.43%.

Among the polymers defined hereinbefore, polymers comprising the following repeating unit are preferred for the polymer employed for the formation of the adhesive layer according to the present invention.

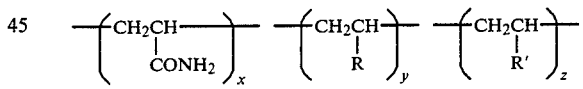

In the above formula, x, y and z mean molar percents for respective groups, and R and R' mean the following substitutents.

| | | |
|---|---|---|
| P-1 | x = 80, y = 8, z = 12, | R = —COOCH$_2$CH$_2$OCOCH$_2$CH$_2$SO$_2$CH=CH$_2$ |
| | | R' = —CONHC(CH$_3$)$_2$CH$_2$COCH$_3$ |
| P-2 | x = 80, y = 8, z = 12, | R = —CONHCH$_2$NHCOCH$_2$CH$_2$SO$_2$CH=CH$_2$ |
| | | R' = —CONHC(CH$_3$)$_2$CH$_2$COCH$_3$ |
| P-3 | x = 80, y = 8, z = 12, | R = —CONHCH$_2$NHCOCH$_2$CH$_2$SO$_2$CH$_2$CH$_2$Cl |
| | | R' = —CONHC(CH$_3$)$_2$CH$_2$COCH$_3$ |
| P-4 | x = 80, y = 8, z = 12, | |

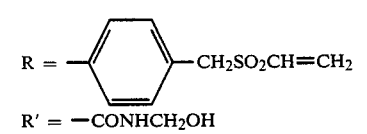

R' = —CONHCH$_2$OH

P-5    x = 70, y = 5, z = 25,

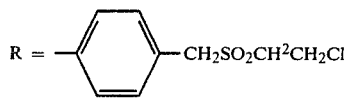

R' = —CON(CH₃)₂

P-6    x = 70, y = 5, z = 25,

R = —CONHCH₂CH₂COON(succinimide)

R' = —CON(CH₃)₂

P-7    x = 50, y = 5, z = 45,

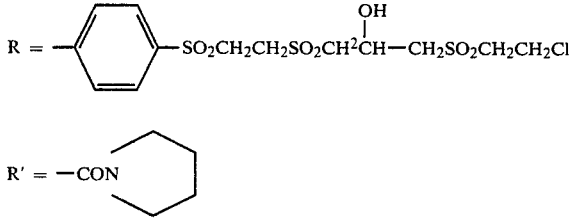

R' = —CON(piperidine)

Processes for the synthesis of the preferably copolymers represented by P-1 and P-3 are illustrated below.

SYNTHESIS EXAMPLE 5

Synthesis of copolymer of N-{[3-(2-chloroethylsulfonyl)propanamido]methyl}acrylamide and acrylamide (corresponding to P-1)

In a reaction vessel, a mixture of 80 ml. of N,N-dimethylformamide, 14.5 g. of 2-[3-(2-chloroethylsulfonyl)-propionyloxy]ethyl acrylate, 34.5 g. of acrylamide and 12.3 g. of N-(1,1-dimethyl-3-oxobutyl)acrylamide was purged with nitrogen gas and heated to 60° C. To the heated mixture was added 0.40 g. of 2,2'-azobis(2,4-dimethylvaleronitrile)[CAS Registry No. 4419-11-8], and the resulting mixture was heated under stirring for 2 hours. Subsequently, 0.20 g. of 2,2'-azobis(2,4-dimethylvaleronitrile) was added to the mixture, and the resulting mixture was further heated under stirring for 2 hours. The mixture was then chilled to 5° C., and after addition of 12 g. of sodium carbonate and 4.9 g. of triethylamine, stirred for one hour. The mixture was then stirred at room temperature for 1 hour. This was introduced into a cellulose tube and subjected to dialysis for 2 days. The remaining solid was freeze-dried to give 56 g. of white polymer: yield 95%.

The vinylsulfonyl content of thus obtained polymer was $0.8 \times 10^{-3}$ eq./g.

SYNTHESIS EXAMPLE 6

Synthesis of copolymer of N-{[3-(2-chloroethylsulfonyl)propanamido]methyl}acrylamide, acrylamide and N-(1,1-dimethyl-2-oxobutyl)acrylamide (corresponding to P-3)

In a 500-ml. reaction vessel, 10.3 g. of the monomer of the synthesis example 2, 25.9 g. of acrylamide, 9.3 g. of N-(1,1-diemthyl-3-oxobutyl)acrylamide, and 160 ml. of 50% aqueous methanol were heated to 60° C. under stirring. To the resulting mixture was added 0.2 g. of 2,2'-azobis(2,4-dimethylvaleronitrile) and after 30 min. further added 0.2 g. of the same reagent. The mixture was then heated under stirring for 1 hour. This was introduced into a cellulose tube and subjected to dialysis for 2 days. The remaining solid was freeze-dried to give 41 g. of the desired white polymer: yield 90%.

The chlorosulfonyl content of thus obtained polymer was $0.7 \times 10^{-3}$ eq./g.

The adhesive layer comprises the copolymer defined as above, and can be formed on a surface of the support in the conventional manner. In the case that the copolymer is water-soluble or hydrophilic, an aqueous solution thereof or a solution thereof in a mixture of water and an organic solvent may be coated over the surface and dried in a conventional manner to form the adhesive layer. In the case that the copolymer is hydrophobic and water-insoluble, a solution thereof in an organic solvent or a mixture of an organic solvent and a small amount of water may be coated over the surface and dried in a conventional manner to form the adhesive layer.

Examples of the organic solvent employable in the above-mentioned procedure include ketones such as acetone and methyl ethyl ketone; alcohols such as methanol and ethanol; N,N-dimethylformamide; dimethylsulfoxide; and ethers such as dimethyl ether and dioxane.

The thickness of the adhesive layer after dryness ranges from approx. 0.1 μm to approx. 3 μm, preferably from approx. 0.2 μm to approx. 2 μm.

DESCRIPTION ON THE MEDIUM FOR ELECTROPHORESIS (POLYACRYLAMIDE GEL MEMBRANE)

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl)acrylamide and diacetonacrylamide, and these compounds may be employed independently or in combination. Acrylamide is most preferable among these acrylamide compounds, and said acrylamide can be also preferably employed in combination with one or more of other acrylamide compounds.

As the crosslinking agent employable to obtain the polyacrylamide gel membrane of the invention, a known crosslinking agent described, for instance, in "Electrophoresis" 1981, 2, 213–228 can be employed singly or in combination. Examples of the crosslinking agent include bifunctional compounds such as N,N'-methylenebisacrylamide (BIS), N,N'-propylenebisacrylamide (PBA), diacrylamide dimethylether (N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamine (BAC). The crosslinking agent can be employed in the amount of approx. 2 to 30 wt.%, preferably approx. 3 to 10 wt.%, based on the total weight of the monomer (i.e., acrylamide compound) and the crosslinking agent. The gel concentration preferably is in the range of approx. 3 to 30 wt/v % (total weight of monomer and crosslinking agent per total volume of gel membrane comprising monomer, crosslinking agent and aqueous medium), the concentration being in accordance with the diffinition indicated by S. Hjerten in "Arch. Biochem. Biophys." 1 (Suppl.), 147 (1962).

As the modifier, a compound containing at least one carbamoyl group is employed. Examples of the modifier include area and formamide. Urea is most preferred. The modifier can be used in an amount of approx. 40 to 60 wt.% based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

A pH buffer agent can be contained in the polyacrylamide gel membrane of the invention. Any buffer agent which is able to buffer a solution to a range of pH 8.0 to 9.0, preferably pH 8.2 to 8.3 can be used. Buffer agents employable in the invention are described in publications such as "Chemistry Handbook, Fundamental Edition" compiled by The Chemical Society of Japan (Maruzen Ltd., Tokyo, 1966) pages 1312–1320; "Modern Electrophoresis" editted by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5, 467 (1966); and "Analytical Biochemistry" 104, pages 300–310 (1966). Examples of the buffer agent include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroxymethyl)methyl]-3-aminopropanesulfonic acid (TAPS) or its Na or K salt; as well as an acid, an alkali, and a salt employable in combination with these compounds. Preferable examples of the buffer agent include Tris, boric acid-EDTA 2Na (pH 8.3).

The polyacrylamide gel membrane of the invention preferably contains a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of the polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 100 wt.%, preferably, approx. 5 to 50 wt.%, based on the total weight of the monomer and crosslinking agent.

The addition of a water-soluble polymer serves to impart elasticity to the gel membrane, and thus modified gel membrane is still elastic even if it is dried. Thus, the gel membrane is so improved as to be free from the brittleness, whereby the gel membrane becomes hardly breakable. Further, the viscosity of the gel membrane can be controlled by selecting the molecular weight and amount of the water-soluble polymer.

The polyacrylamide gel membrane preferably contain agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO 82/02599, U.S. Pat. No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel-forming solution can be controlled through changing the temperature of the solution, whereby suppressing flowability of the solution as well as facilitating the formation of the gel membrane.

The polyacrylamide gel membrane of the element of the invention is formed by radical crosslinking polymerization between the monomer such as acrylamide with the bifunctional compound (crosslinking agent) in an aqueous medium in which the water-soluble polymer and agarose are dissolved almost homogeneously. The gel is assumed to have a structure in which the water-soluble polymer and agarose are dispersed in the three dimensional crosslinked polymer formed by the reaction of the monomer and cross-linking agent, and the water-soluble polymer and agarose are dispersed and are further entangled with the three dimensional crosslinked polymer structure.

The crosslinking polymerization can be initiated by a known method, for instance, in the presence of a peroxide and/or under irradiation of ultra-violet rays. The reaction can be further accelerated by heat and irradiation with ultra-violet rays.

As the polymerization catalyst, a known low temperature-polymerization initiator such as those described in "Electrophoresis" 1981, 2, 213-219, ibid. 1981, 2, 220-228; and "Modern Electrophoresis" editted by Aoki & Nagai (Hirokawa Shoten, 1973) can be used. Examples of the initiator include a mixture of β-dimethylaminopropionitrile (DMAP) and ammonium peroxodisulfate, a mixture of N,N,N',N'-tetramethylethylenediamine (TEMED) and ammonium peroxodisulfate, a mixture of TEMED and riboflavin, a combination of a mixture of TEMED, riboflavin and hydrogen peroxide, and irradiation with ultra-violet rays. The radical reaction initiator can be employed in the amount of approx. 0.3 to 5 wt. %, preferably approx. 0.5 to 3 wt. %, based on the total amount of the monomer and crosslinking agent.

The polyacrylamide gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

A polyol compound such as glycerol or ethylene glycol can be contained in the polyacrylamide gel membrane of the element of the invention as a wetting agent. The polyol compound can be introduced in an amount of approx. 5 to 40 wt.% based on the volume of the aqueous gel membrane. Glycerol is particularly preferable among the polyol compounds. The addition of the wetting agent serves to keep the gel membrane from excessive dryness possibly caused by evaporation of water during storage of the medium, whereby preventing the medium from turning brittle or cracking caused by the excessive dryness. Thus, the improvement of physical properties of the gel membrane is accomplished.

The polyacrylamide gel membrane of the element of the invention can be prepared by a process in which a gel forming solution is coated by a known method on an electric insulation support having a smooth hydrophilic surface, and the gel forming solution is crosslinked to polymerization thereon. Some examples of the support are mentioned hereinbefore. In more detail, examples of the support include glass plate, hydrophilic polymers in the form of plate or sheet, and other polymers (e.g., polyethylene terephthalate, polycarbonate of bisphenol A, polyvinyl chloride, vinylidene chloride-vinyl chloride copolymer, polymethylmethacrylate, polyethylene, polypropylene, cellulose acetate, and cellulose acetate propionate) in the form of plate or sheet, a surface of which is made hydrophilic by a known surface treatment. Examples of the treatment employable to make the surface of these polymers hydrophilic include known methods such as irradiation with ultra-violet rays, glow discharge treatment, corona discharge treatment, flame treatment, electron beam treatment, chemical etching, or electrochemical etching. Nevertheless, the hydrophilic surface is not necessarily provided on the support, and the above-mentioned polymer sheet can be employed with no hydrophilic treatment.

In the case that the gel forming solution is crosslinked to polymerization on the surface of the support, the surface of the gel forming solution can be covered with a covering material such as a film, sheet, or plate. The same material as employable for the support can be employed as the covering material. The covering material has thickness of not more than 200 μm, and preferably has approx. 4-200 μm, from the practical viewpoint.

In the case that the covering material is thick (e.g., approx. 70-300 μm), the element of the present invention can be prepared by the following steps: the gel forming solution is first coated on the covering material and crosslinked thereon to form the desired gel medium layer, and then a support having the adhesive layer mentioned hereinbefore is provied on the gel medium layer.

The gel membrane of the invention can be employed for the horizontal or vertical electrophoresis, disc electrophoresis, etc. by known methods described, for instance, in the aforementioned texts.

The medium for electrophoresis provided to the element of the present invention is strongly bound to the support through the provision of the specific adhesive layer. Accordingly, the element for electrophoresis of the present invention is always kept in the form of an integrated unit in the course of ordinary operations. For this reason, the complicated operations conventionally required in the electrophoresis for determination of base sequence of DNA, etc. can be simplified by the use of the element for electrophoresis according to the present invention. Moreover, the electrophoresis operation and dyeing operation can be performed by the integrated structure comprising the support and the gel membrane provided thereon.

The present invention will be more clearly understood with reference to the following examples.

EXAMPLE 1

The polymer set forth in Table 1 was coated on a polyethylene terephthalate (PET) sheet (i.e., support) having been made hydrophilic by irradiation of ultra-violet rays and dried to approx. 110° C. to form an adhesive layer of approx. 0.5 μm thick (solid portion).

TABLE 1

| Composition of Coating Solution for the Formation of Adhesive Layer | | |
|---|---|---|
| Sample No. | Polymer | Polymer Content |
| 1 | P-A | 5 g. |
| 2 | P-B | 4.5 g. |
|   | BIS | 0.5 g. |
| 3 | P-1 | 5 g. |
| 4 | P-3 | 5 g. |
| 5 | P-6 | 5 g. |

Remarks: The polymer content means that water was added to the polymer in the indicated amount to give 100 ml. of aqueous polymer solution. BIS means N,N'-methylenebisacrylamide. P-1, P-3, and P-5 mean the polymers respectively illustrated hereinbefore. P-A and P-B are both two units copolymer having the following repeating units:

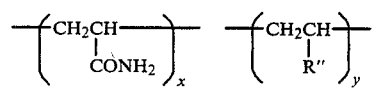

P-A: x=80, y=20, R"=CONHC(CH$_3$)$_2$CH$_2$COCH$_3$
P-B: x=87, y=13, R"=CONHC(CH$_3$)$_2$CH$_2$COCH$_3$

The adhesiveness between the PET sheet (support) and the adhesive layer was evaluated by a cross-cut method. As a result, it was observed that the samples 3, 4 and 5 (according to the present invention) were satisfactory in the adhesiveness, while the samples 1 and 2 (control samples) showed separation of the adhesive layer from the support in not a few portions.

On the adhesive layer provided on the support was formed a polyacrylamide gel membrane of 0.5 mm thick by coating an aqueous solution containing 11.87 g. of acrylamide, 0.63 g. of BIS, 42 g. of urea, 1.08 g. of tris(hydroxymethyl)aminomethane [CAS Registry No. 77-86-1], 0.55 g. of boric acid, and 93 mg of EDTA Na salt in 100 ml. volume after addition of 1.3 ml of ammonium peroxodisulfate (5 weight %) and 33 μl. of TEMED, both being the polymerization initiators. Thus, an element for electrophoresis was obtained.

The adhesiveness between the polyacrylamide gel membrane and the support in the element for electrophoresis was evaluated by pressing the gel membrane with a finger. As a result, it was observed that the samples 3, 4 and 5 (according to the present invention) were satisfactory in the adhesiveness, while the samples 1 and 2 (control samples) were lower than the the samples 3, 4 and 5 in the adhesiveness.

EXAMPLE 2

The PET sheet provided with the adhesive layer was prepared in the same manner as in Example 1 using the polymer set forth in Table 1. On the adhesive layer was formed a polyacrylamide gel membrane of 0.5 mm thick by coating an aqueous solution containing 11.87 g. of acrylamide, 0.63 g. of BIS, 0.3 g. of agarose (low electroendosmosis, gelation temperature 36° C.), 2.5 g. of polyacrylamide, 42 g. of urea, 1.08 g. of tris(hydroxymethyl)aminomethane, 0.55 g. of boric acid, and 93 mg. of EDTA Na salt in 100 ml. volume after addition of 1.3 ml of ammonium peroxodisulfate (5 weight %) and 33 μl. of TEMED, both being the polymerization initiators. Thus, an element for electrophoresis was obtained.

A sample ($^{32}$P-DNA cleaved by Maxam-Gilbert method) was electrophoresed on the polyacrylamide gel membrane for sequencing the DNA. The element was then immersed in 10% aqueous acetic acid solution for 1 hour so as to remove the urea and fix the resolved substance to the membrane. In this immersing stage, the adhesiveness between the support and the polyacrylamide gel membrane was observed for each element.

In the sample 1 (control sample), the gel membrane separated rather easily from the support immediately after the element was immersed in the solution. In the sample 2 (control sample), a certain portion of the gel membrane separated in the solution, though other portion of the membrane was still bound to the support.

In contrast, all of the gel membranes in the samples 3, 4, and 5 (according to the present invention) were completely bound to the support during the immesing stage as well as after being subjected to the subsequent drying procedure.

The samples 3, 4 and 5 were then subjected to the conventional autoradiographic process. No unsatisfactory results were observed in the autoradiographic process.

EXAMPLE 3

A polyacrylamide gel membrane was formed on the adhesive layer of the PET sheet to prepare an element for electrophoresis in the same manner as in Example 2. The gel membrane was cut together with the support, and the cut face (section) of the gel membrane was observed. Partial separation of the gel membrane from the support was observed in the samples 1 and 2 (control samples), while no separation was observed in the samples 3, 4 and 5 (according to the present invention). This means that the element for electrophoresis according to the invention can be cut with no unfavorable separation between the gel membrane and the support.

We claim:

1. An element for electrophoresis comprising the following three-layer structure laminated in the order:
   (I) a support layer;
   (II) an adhesive layer comprising a polymer having at least one repeating unit selected from the group consisting of:
   (1) a repeating unit having the formula (1):

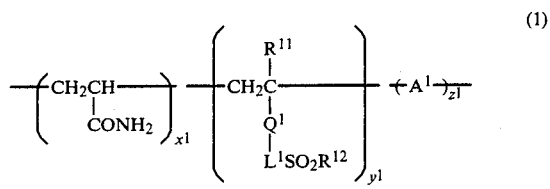

in which $R^{11}$ is the hydrogen atom or an alkyl group containing 1–6 carbon atoms; $Q^1$ is —COO—, —CON($R^{11}$)—, or an arylene group containing 6–10 carbons atoms; $L^1$ is a divalent group containing at least one linkage selected from the group consisting of —COO— and —CON($R^{11}$)— and containing 3–15 carbon atoms, or a divalent group containing at least one linkage selected from the group consisting of —O—, —N($R^{11}$)—, —CO—, —SO—, —SO$_2$—, —SO$_3$—, —SO$_2$N($R^{11}$)—, —N($R^{11}$)CON($R^{11}$)— and —N($R^{11}$)COO—, and containing 1–12 carbon atoms, in which $R^{11}$ has the same meaning as defined above; $R^{12}$ is —CH=CH$_2$ or —CH$_2$CH$_2$X$^1$, in which $X^1$ is a substituent replaceable with a nucleophilic troup or releasable in the form of HX$^1$ by a base; $A^1$ is a divalent group derived from an ethylenic unsaturated monomer copolymerizable with monomers forming other unit portions; and $x^1$, $y^1$ and $z^1$ all representing molar percents range from 0 to 99, from 1 to 99, and from 1 to 99, respectively;

(2) a repeating unit having the formula (2):

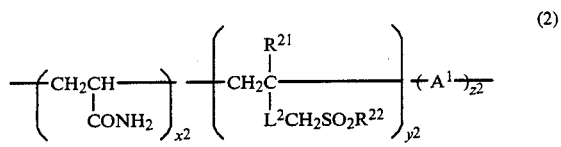

in which $R^{21}$ is the hydrogen atom or an alkyl group containing 1–6 carbon atoms; $R^{22}$ is —CH=CH$_2$ or —CH$_2$CH$_2$X$^2$, in which $X^2$ is a substituent replaceable with a nucleophilic group or releasable in the form of HX$^2$ by a base; $L^2$ is a divalent group selected from the group consisting of an alkylene group containing 1–6 carbon atoms, an arylene group containing 6–12 carbon atoms, —COZ$^2$—, and —COZ$^2$R$^{23}$—, in which $R^{23}$ is an alkylene group containing 1–6 carbon atoms, or an arylene group containing 6–12 carbon atoms, and $Z^2$ is the oxygen atom or NH; $A^2$ is a divalent group derived from an ethylenic unsaturated monomer copolymerizable with monomers forming other unit portions; and $x^2$, $y^2$ and $z^2$ all representing molar percents range from 0 to 99, from 1 to 99, and from 1 to 99, respectively; and (3) a repeating unit having the formula (3):

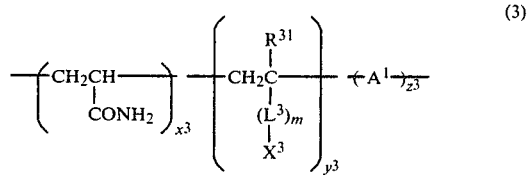

in which $R^{31}$ is the hydrogen atom or an alkyl group containing 1–6 carbon atoms; $L^3$ is a divalent linkage group containing 1–20 carbon atoms; $X^3$ is an active ester; $A^3$ is a divalent group derived from an ethylenic unsaturated monomer copolymerizable with monomers forming other unit portions; $x^3$, $y^3$ and $z^3$ all representing molar percents range from 0 to 99, from 1 to 99, and from 1 to 99, respectively; and m is 0 or 1; and (III) a medium layer for electrophoresis comprising an aqueous polyacrylamide gel formed by cross-linking polymerization of an acrylamide compound and a crosslinking agent in the presence of water, a water-soluble polymer, agarose and a compound containing at least one carbamoyl group serving as modifier.

2. The element for electrophoresis as claimed in claim 1, in which said compound serving as modifier is urea or formamide.

3. The element for electrophoresis as claimed in claim 1, in which said support layer is made of a plastic material sheet.

4. The element for electrophoresis as claimed in claim 3, in which the plastic material sheet is a polyethylene terephthalate sheet.

5. The element for electrophoresis as claimed in claim 1, in which the adhesive layer consists essentially of a polymer having the formula (1).

6. The element for electrophoresis as claimed in claim 1 in which said water-soluble polymer is contained in the amount of 2 to 100 wt.% based on the polyacrylamide solid and said agarose is contained in the aqueous polyacrylamide gel in an amount of 0.2 to 2 wt/v %.

* * * * *